(12) United States Patent
Kraemer (10) Patent No.: US 7,788,756 B2
(45) Date of Patent: Sep. 7, 2010

(54) BRUSH PART FOR ELECTRIC TOOTHBRUSH

(75) Inventor: Hans Kraemer, Buehl (DE)

(73) Assignee: GlaxoSmithKline Consumer Healthcare GmbH & Co. KG, Buehl (Baden) (DE)

( * ) Notice: Subject to any disclaimer, the term of this patent is extended or adjusted under 35 U.S.C. 154(b) by 1449 days.

(21) Appl. No.: 10/433,850

(22) PCT Filed: Dec. 3, 2001

(86) PCT No.: PCT/EP01/14040

§ 371 (c)(1),
(2), (4) Date: Sep. 28, 2005

(87) PCT Pub. No.: WO02/45617

PCT Pub. Date: Jun. 13, 2002

(65) Prior Publication Data

US 2006/0248667 A1    Nov. 9, 2006

(30) Foreign Application Priority Data

Dec. 7, 2000   (GB) ................................. 0029813.3
Feb. 10, 2001  (GB) ................................. 0103340.6

(51) Int. Cl.
*A61C 17/34* (2006.01)
*A46B 7/08* (2006.01)
(52) U.S. Cl. ..................... 15/28; 15/22.1; 15/DIG. 5
(58) Field of Classification Search ............... 15/22.1, 15/28, 180, DIG. 5, 22.2; D4/104
See application file for complete search history.

(56) References Cited

U.S. PATENT DOCUMENTS

| 4,114,225 | A  | * | 9/1978  | Malish et al. ............ 15/230.17 |
| 6,016,587 | A  | * | 1/2000  | Savitt et al. ................. 15/167.1 |
| 6,363,565 | B1 | * | 4/2002  | Paffrath ........................... 15/28 |
| 2002/0157198 | A1 | * | 10/2002 | Biro et al. ....................... 15/22.1 |

FOREIGN PATENT DOCUMENTS

DE    8807968    10/1989
EP    0765642    4/1997

* cited by examiner

*Primary Examiner*—Randall Chin
(74) *Attorney, Agent, or Firm*—Nora Stein-Fernandez; Theodore R. Furman (57) ABSTRACT

A brush part for an electric toothbrush in which tufts of bristles are arranged in polygons, and in which the tufts of bristles lean, either around the polygons or inwardly and outwardly, so that the tuft alignments converge and preferably cross.

12 Claims, 9 Drawing Sheets

BRUSH PART FOR ELECTRIC TOOTHBRUSH

This invention relates to bristles for electric toothbrushes, in particular to bristle clusters for electric toothbrushes.

Electric toothbrushes generally comprise a handle which contains inter alia a power supply and a drive motor, a neck extending from the handle and containing a transmission means e.g. a drive shaft, and a brush part which includes a bristle holder mounted thereon for rotary motion about a rotation axis, and connected by the transmission means to the motor. A cluster of tufts of bristles is mounted on a surface of the holder, extending generally in a bristle direction, with their end closest to the bristle holder, i.e. their base end, set in the holder and their distal end furthest from the holder. Generally the bristle tufts extend generally parallel to the rotation axis. Generally the handle, neck and bristle holder lie along a longitudinal axis direction, and the rotation axis is at a transverse angle to this axis direction, e.g. generally at right angles. Commonly the bristle holder is replaceable on the handle, often together with the neck. Often the rotary motion is oscillatory, i.e. motion involving reciprocal angular displacement about a mean position, and the term "rotary" herein includes oscillatory rotary motion. Sometimes the rotary motion also involves a reciprocal back and forth movement of the bristle holder along the rotational axis direction.

Numerous constructions of electric toothbrush of this type are known, for example the applicant's own Dr BEST "E-FLEX" (™) electric toothbrush launched in 2000 which has a brush part mounted for oscillatory rotary motion.

Electric toothbrushes are known from U.S. Pat. No. 4,608,968 and DE-G-88 07 968.6 in which the tufts of bristles are arranged leaning outwardly relative to the rotation axis, with progressively less steeply leaning tufts toward the centre of the cluster, and with tufts at the centre of the bristle cluster arranged parallel to the rotation axis. EP-A-0 765 642 discloses electric toothbrush tuft clusters which have their bristle tufts inclined an a non-zero angle to the rotation axis, leaning toward a central longitudinal plane of the toothbrush. WO-A-0041592 discloses an oscillatory rotary electric toothbrush bristle cluster in which the tufts of bristles are inwardly leaning toward the rotation axis in a conical or pyramidal arrangement.

For "manual" toothbrushes, i.e. toothbrushes without an electric motor and which operate solely by the motion of the user's hand, bristle configurations are known in which as viewed from certain directions, particularly from the side, the bristle tufts, or their extrapolation, are seen to converge and cross. This is for example disclosed in DE-A-633 556, DE-G-82 02 897.6, FR-A-683 311, FR-A-2,624,360, U.S. Pat. Nos. 2,242,743, 3,085,273, 4,010,509, 4,081,876, 4,776,054, 5,274,873 and WO-A-99/23910. DE-A-44 12 301 and DE-A-35 44 256 disclose electric toothbrushes with bristles which are crossed in an "X" arrangement.

These known bristle clusters do not optimise tooth cleaning, particularly the cleaning of the interproximal spaces between the teeth where dirt can collect. It is an object of the present invention to provide an improved bristle cluster for electric toothbrushes of the above-described type.

According to a first aspect of this invention a brush part for an electric toothbrush is provided which includes a bristle holder mounted for rotary motion about a rotation axis, a plurality of first tufts projecting from a surface of the bristle holder and having their bases arranged in a polygon around the rotation axis and leaning outwardly away from the rotation axis so that their distal end is further out from the rotation axis than their base, and a plurality of second tufts projecting from a surface of the bristle holder and having their bases arranged in a polygon around the rotation axis, characterised by:

the first and second tufts having their bases at different radial distances from the rotation axis, the first and second tufts oriented relative to the rotation axis such that at a point along their base-distal end length the first and second tufts are respectively at radial distances from the rotation axis with a difference in their respective radial distances less than the difference in the respective radial distances of their bases from the rotation axis.

According to a second aspect of this invention a brush part for an electric toothbrush is provided which includes a bristle holder mounted for rotary motion about a rotation axis, a plurality of first tufts projecting from a surface of the bristle holder and having their bases arranged in a polygon around the rotation axis, and a plurality of second tufts projecting from a surface of the bristle holder and having their bases arranged in a polygon around the rotation axis, characterised by:

the first tufts comprising an inner polygon in which at least one tuft is mounted inclined at an angle such that the distal end of the tuft is further around the polygon than the base end in a first direction, and the second tufts comprising an outer polygon in which at least one tuft is mounted inclined at an angle such that the distal end of the tuft is further around the polygon than the base end, in a second direction opposite to the first direction.

In both the first and second aspects of this invention the bristle holder is connectable to a toothbrush handle containing an electric drive motor and capable of being driven in rotary motion by the drive motor when connected thereto about a rotation axis generally transverse to an axis between the brush part and the handle. Such rotary motion may be oscilatory rotary motion.

Preferably in the toothbrush head of the first aspect of this invention the bases of the second tufts are located at a greater radial distance from the rotation axis than are the bases of the first tufts.

Preferably in this brush part of the first aspect of the invention at a point along their base-distal end length the first and second tufts are respectively at the same radial distances from the rotation axis, i.e. so that the difference in their respective radial distances at this point is zero. Preferably further distally along the base-distal length from this point the difference in their respective radial distances of the first and second tufts increases.

Preferably in this brush part of the first aspect of the invention the first and second tufts are circumferentially adjacent to each other at the point of minimum difference, e.g. of zero difference, in their respective radial distances, on a circle centred on the rotation axis.

One embodiment of this brush part of the first aspect of the invention comprises a plurality of second tufts having their bases further radially out from the rotation axis than the bases of the first tufts, and aligned parallel to the rotation axis.

A second embodiment of this brush part of the first aspect of the invention comprises a plurality of second tufts having their bases further radially out from the rotation axis than the bases of the first tufts, and leaning inwardly toward the rotation axis so that their distal ends are at less distance radially from the rotation axis than their base.

A third embodiment of this brush part of the first aspect of the invention comprises a plurality of second tufts having their bases further radially out from the rotation axis than the bases of the first tufts, and leaning outwardly away from the rotation axis so that their distal end is further out from the rotation axis than their base, but at a lesser angle of lean relative to the rotation axis than the first tufts.

Preferably in this brush part of the first aspect of the invention the distal ends of the first tufts are further radially out than the distal ends of the first tufts, although the distal ends of the first tufts may be at the same or lesser radial distance than the distal ends of the second tufts from the rotation axis. This allows a preferred arrangement in which the respective lean of the outwardly leaning first tufts and the orientation of the second tufts is such that as viewed along a line tangential to a circle centred on the rotation axis and mid way between the bases of the first and second tufts circumferentially adjacent first and second tufts as seen superimposed are seen to cross each other. In such an arrangement the tufts may cross at the mid point between the base and the distal ends along the tufts, or closer to the base or closer to the distal ends of the tufts.

Preferably in this brush part of the first aspect of the invention the second tufts also have their bases arranged in a polygon around the rotation axis in which in such a polygon the bases of the second tufts lie outside and preferably concentric with the polygon of bases of the first tufts. Suitably there may be one or more such polygon of first tufts and/or one or more such polygon of second tufts.

For example in this brush part of the first aspect of the invention there may be two or more polygons of first tufts, one within the other preferably concentrically about the rotation axis, the respective first tufts in these polygons leaning outwardly at the same or different angle relative to the rotation axis, and for example having their first tufts arranged on radii from the rotation axis. In such an arrangement there may for example also be two or more polygons of second tufts, one within the other. A preferred arrangement of first and second tufts comprises, proceeding radially outward from the rotation axis: a polygon of bases of first tufts; a polygon of bases of second tufts oriented parallel to the rotation axis; another polygon of bases of first tufts; another polygon of bases of second tufts oriented parallel to the rotation axis.

In this brush part of the first aspect of the invention a polygon of second tufts may be the radially outermost tufts of the cluster of bristle tufts.

Preferably in this brush part of the first aspect of the invention the angle relative to the rotation axis at which the outwardly leaning first tufts may lean may be between 2.5 to 35°, preferably between 5 to 10°, for example typically around 8-10°.

If in this brush part of the first aspect of the invention the second tufts are inwardly leaning as mentioned above, they may be combined in the cluster with first tufts which lean outwardly at between 2.5 to 35°, preferably between 5 to 25°, for example between 10 to 15°, typically around 12°, and the respective first and second tufts may lean respectively outwardly and inwardly at the same or different angles relative to the rotation axis.

In the clusters described above in this brush part of the first aspect of the invention where a polygon of bases of outwardly leaning first tufts is within a polygon of bases of second tufts, the tufts may be arranged so that first tufts are radially (relative to the rotation axis) adjacent to a gap between two circumferentially adjacent second tufts. Such an arrangement allows an outwardly leaning first tuft to lean outwardly between flanking pairs of second tufts which are oriented substantially parallel to the rotation axis, and a second tuft oriented substantially parallel to the rotation axis may be between flanking pairs of outwardly leaning first tufts. It alternatively allows an outwardly leaning first tuft to lean outwardly between flanking pairs of inwardly leaning second tufts, and an inwardly leaning second tuft to lean inwardly between flanking pairs of outwardly leaning first tufts. Alternatively it allows an outwardly leaning first tuft to lean outwardly between flanking pairs of second tufts which also lean outwardly, and a second tuft leaning outwardly to be between flanking pairs of outwardly leaning first tufts. With such arrangements of first and second tufts it is appropriate that there are the same numbers of tufts in the respective inner first and outer second polygons.

Alternatively in this brush part of the first aspect of the invention the outwardly leaning first tufts may be arranged in groups of two or more circumferentially adjacent first tufts, and/or the second tufts may be arranged in groups of two or more circumferentially adjacent second tufts. In such arrangements, such groups of first tufts may be circumferentially between pairs of second tufts, or vice versa.

Outwardly and inwardly leaning tufts in this brush part of the first aspect of the invention may lean inwardly along radii centred at the rotation axis, so that the tufts lean respectively straight away from and toward the rotation axis, i.e. perpendicular to the direction of rotation. In such an arrangement the respective directions of lean in projection converge radially on the axis of rotation. Alternatively the respective directions of lean in projection may be along lines parallel to each other, preferably with a parallel line between the directions of lean passing through the axis of rotation.

Turning now to the brush part of the second aspect of the invention, at least one tuft in each of the first and second polygons is inclined around the polygon as described, and preferably all of the tufts in the polygons are inclined.

In this brush part of the second aspect of the invention, relative to the axis of rotation the angle at which the at least one, or preferably all the tufts, are inclined such that the end of the tuft which is furthest from the surface of the bristle holder is further around the polygon than the end of the tuft which is mounted in the surface may suitably be in the range 1 to 30°, typically 3 to 15°, especially 7-12°. If the ends of the tuft which are mounted in the bristle holder lie in a plane, e.g. if the surface of the bristle holder is a flat surface defining such a plane, then this angle may be in the range 89 to 60°, typically 87 to 80°, especially 83-78° to this plane.

In this brush part of the second aspect of the invention the inclined tuft(s) may be aligned in a direction substantially parallel to an adjacent side of the polygon. Alternatively the tuft(s) may be inclined inwardly or outwardly, relative to the centre of the polygon, for example in a direction in the range 0°-30°, preferably 0°-10°, inwardly or preferably outwardly angled relative to the centre of the polygon as viewed in plan, relative to the direction of an adjacent side of the polygon. The consequence of this latter inclination is that the end of the tuft which is furthest from the surface of the bristle holder is further out or in relative to the centre of the polygon, than is the end of the tuft which is mounted in the surface.

In the inner first and outer second polygons in this brush part of the second aspect of the invention, the respective inclined tufts of bristles are inclined in respective opposite directions around the polygon. For example the tuft(s) in the inner first polygon may be inclined such that the distal end of the tuft(s) is further around the polygon than the base end of the tuft in an anti-clockwise direction, whilst the tuft(s) in the outer second polygon may be inclined such that the distal end is further around the polygon than the base end in a clockwise direction, or vice versa.

In such first and second polygons of this brush part of the second aspect of the invention, the angles of inclination in the respective directions around the polygon may be the same or different, and/or the tuft(s) of the inner first and outer second polygons may differ in whether they are aligned with an adjacent side of the polygon or whether they are inclined inwardly or outwardly. For example the tuft(s) of the inner polygon may be inclined at a smaller angle relative to the axis of rotation in the direction around the polygon than the outer polygon, For example the tufts of the inner polygon may be inclined parallel to an adjacent side of the polygon, whilst the tufts of the outer polygon are inclined outwardly.

As described herein the position of a tuft relative to the axis of rotation refers to the position of the centre of its base or distal end. In the brush part of both the first and second aspects of the invention the above described polygons are preferably regular polygons. In such above described inner and outer polygons of tufts there may be for example be the same or different numbers of first and second tufts in the respective inner and outer polygons. In both the first and second aspects of the invention the distal ends of the first and second tufts of the cluster may all be at the same distance from the surface of the bristle holder, e.g. so that the distal ends lie in a plane perpendicular to the rotation axis.

In both the first and second aspects of this invention the first and second tufts may be combined in the cluster with one or more other kinds of tufts, called generally herein "third tufts". Such one or more third tuft may be provided in the cluster for example to create a suitable density of tufts for effective tooth cleaning. Such one or more third tuft may be located at any position in the cluster. For example the cluster may comprise one or more polygon of tufts which include both one or more first tuft and one or more third tuft, and/or one or more polygon of tufts which include both one or more second tuft and one or more third tuft. Alternatively such third tufts may be provided in one or more third polygon which includes third tufts, and for example may contain only third tufts. Such third polygon may have a common centre with the above-mentioned one or two polygons. For example such third polygon may be situated within and surrounded by, or outside of and surrounding, the above-mentioned first and second polygons. For example such a third polygon may be within and surrounded by the innermost of a polygon of first or second tufts. For example such third polygon may be radially between the inner first and outer second polygon. There may for example be a single third tuft at the centre of the first or second polygon.

For example in the brush head of both the first and second aspects of the invention such one or more third tuft may comprise one or more tuft aligned parallel with the rotation axis. For example in the first aspect of the invention such one or more third tuft may comprise one or more tuft leaning in the direction of rotation, e.g. as disclosed in EP-A-0 765 642, or leaning inwardly toward the rotation axis e.g. as disclosed in WO-A-0041592, the contents of which are incorporated by reference.

For example in the brush part of the first aspect of this invention, two such above-described respective inner and outer polygons of respectively first and second tufts may comprise the two outermost tufts of the cluster, and there may be such third tufts within the inner polygon, e.g. forming an innermost third polygon. The third tufts may for example extend further from the surface than do the first and second tufts, which all may have their distal ends at the same perpendicular distance from surface. In this arrangement the third tufts form a central peak, and the distal ends of the third tufts may be cut obliquely to their length.

For example in the brush part of the second aspect of the invention the cluster of bristles may comprise three polygons of tufts, being a first inner polygon and a second outermost polygon surrounding the first inner polygon, with all of the tufts in these first and second polygons being inclined at an angle such that the distal end of the tuft is further around the polygon than the base end but in respectively opposite directions around the polygon, together with a third innermost polygon of tufts within the first inner polygon, the tufts of this innermost third polygon being parallel to the axis of rotation. These various polygons preferably have a common centre. In this embodiment there may also be a single third tuft at the centre of the polygons being aligned parallel to the axis of rotation.

In the brush heads of both aspects of this invention the number of tufts in the various above-mentioned polygons may be determined in practice by the dimensions of the tufts and the bristle holder. Typically bristle tufts as used in electric toothbrushes have a cross sectional dimension of ca. 1 mm, and the width of the bristle surface of a rotatable bristle holder of an electric toothbrush is ca. 10-12 mm. Typically the outermost polygon of tufts contains 10-20 tufts. Typically a polygon immediately radially inward of such an outermost polygon of tufts 8-12 tufts. The above-mentioned polygons in both aspects of the present invention are preferably regular polygons.

The ends of the bristles remote from the surface of the bristle holder may be profiled in various ways.

For example as mentioned above in the brush part of the first aspect of this invention, an innermost polygon of third tufts may for example extend further from the surface than do the first and second tufts, which all may have their distal ends at the same perpendicular distance from surface. In this arrangement the third tufts form a central peak, and the distal ends of the third tufts may be cut obliquely to their length.

For example in the brush part of the second aspect of this invention the ends of all the tufts of the polygon(s) in which at least one tuft is mounted inclined at an angle such that the distal end of the tuft is further around the polygon than the base end, may be in a plane perpendicular to the axis of rotation.

Alternatively for example in the brush part of the second aspect of this invention the ends of the tufts may form a central peak. For example such a cluster may comprise first and second inner and outer polygons of tufts including the inclined tuft(s), with an innermost polygon of third tufts aligned parallel to the rotation axis, with optionally a single central tuft, and the ends of the bristles of the innermost polygon and of the central tuft (if present) may be profiled to form a central peak. The ends of the tufts of the innermost polygon may be cut obliquely to their length so as to incline upwards toward the centre of the polygon. In such a central peak the ends of the tufts may be profiled into a generally conical shape with its apex pointing away from the bristle surface.

Alternatively in the brush part of the second aspect of this invention the ends of the tufts may form a concavity about the centre of the cluster, and for example the ends of the tufts may form a central peak about the centre of this concavity so that the height of the polygons dips between the outermost and innermost polygons. The ends of the tufts of this peak may be profiled into a generally domed shape, e.g. a generally hemispherical dome with its radius pointing away from the bristle surface. For example in such an arrangement the tufts of the innermost polygon may be higher that the tufts of the outermost polygon by ca. 0.5-1.5 mm, and the tufts of the intermediate polygon may be lower that the tufts of the outermost polygon by ca. 0.5-1.5 mm.

For example alternatively in another embodiment of the brush part of the second aspect of this invention the ends of all the tufts may be profiled in a concave generally cylindrical surface having the longitudinal axis of the cylinder aligned perpendicular to the axis of rotation. A typical width for the cluster of the brush part is ca. 10-12.5 mm measured perpendicular to the bristle direction. With such a width a suitable radius of curvature of the cross section of such a cylindrical surface is ca. 8-12 mm, e.g. 10-11 mm.

The term "conical" as used herein including shapes with other than true circular cross sections across the axis of rotation e.g. pyramid shapes, and with curved sides e.g. ogival shapes. The term "sphere" and derived terms as used herein including shapes with other than true circular cross sections e.g. oblate spheroids and ellipsoidal shapes. The term "cylindrical" as used herein includes true cylinders i.e. a shape having straight longitudinal sides and a circular cross section, with the longitudinal axis of the cylinder passing through the centre of the circular section. The term also includes distorted cylinders, e.g. shapes with convex bulging longitudinal sides e.g. "barrel" shapes, and shapes with concave sides, i.e. wider at the cylinder ends than at a waist partway between the ends, provided however that the radius of curvature of the convex or concave sides is greater than the radius of curvature of the cross section shape. Also the term "cylinder" includes such shapes with oval or oblate circular, or polygonal, including polygonal with rounded corners or sides, cross section.

The brush part of this invention appears to be suitable for all electric toothbrushes in which the bristle holder is mounted for and moveable in rotary motion about an axis transverse to, preferably substantially perpendicular to, the longitudinal head—handle axis of the toothbrush, substantially parallel to the bristle direction, and passing through or close to the centre of the bristle pattern. Preferably the rotary motion is oscillatory, i.e. involving rotation through an angle in one rotary direction, alternating with rotation through substantially the same angle in the opposite rotational direction.

Preferably this rotary motion is combined with reciprocal motion of the bristles along the bristle direction, i.e. up and down the bristle direction. For example the motion of the bristle holder, combining such oscillatory rotary and reciprocal motion, may be reciprocally helical. Suitable drive mechanisms to drive the bristle holder in this way are known, for example in U.S. Pat. No. 5,577,285, WO-A-01/06946 and WO-A-01/06947, the contents of which are included herein by reference. The drive speeds, amplitudes, and oscillation frequencies, e.g. ca. 3000-6000 rpm achievable by means of such known drive mechanisms are believed to be suitable for the brush part of both aspects of the present invention.

Therefore the invention further provides an electric toothbrush having a brush part as described above. For example the brush part of this invention may be connectable, preferably replaceably connectable, to a toothbrush handle containing an electric drive motor which when so connected can drive the brush part in the above-described rotary motion. For this purpose the brush part suitably comprises part of a toothbrush head which is itself provided with connection means by which the brush part may be connected to the handle and to the motor. The brush part may for example be rotatably mounted on the toothbrush head, for example by known means, such as an axle mounting, many types of which are known. The connection means may comprise a hollow neck part extending longitudinally between the head and the handle and enclosing a drive shaft by which the motor can drive the brush part via suitable transmission means. The neck part may itself be connectable, preferably replaceably, at its end remote from the head, to the handle in a manner which also connects the drive shaft to the motor. Alternatively the head may itself be connectable, preferably replaceably, to the neck part at its end remote from the handle, to the neck part in a manner which also connects the drive shaft to the brush part.

Many means by which the motor can drive the shaft, and the shaft can drive the brush part, to achieve such motion are known.

Generally an electric toothbrush is an elongate structure which comprises a head (including the brush part) and handle disposed along a head—handle axis being the length of the toothbrush, and for example if the bristle holder performs oscillatory rotary motion the longitudinal axis of the part cylindrical surface may oscillate about a mean alignment perpendicular to the length of the electric toothbrush.

The toothbrush bristle holder and the bristles themselves of the brush part of this invention may be made of materials which are conventional in the field of electric toothbrush manufacture, e.g. respectively of plastics materials and bristles of nylon, e.g. Tynex™ material fibres. The plastics material parts of the bristle holder and other plastics material parts of the toothbrush may be made by an injection moulding process, and accordingly the invention further provides a process for making a toothbrush as described herein, comprising injection moulding of plastics material. Further the invention provides an injection mould suitable for use in such a process.

The bristle cluster of this invention is believed to provide improved tooth cleaning relative to know bristle clusters.

The invention will now be described by way of example only with reference to the following figures which show.

Figure 1:
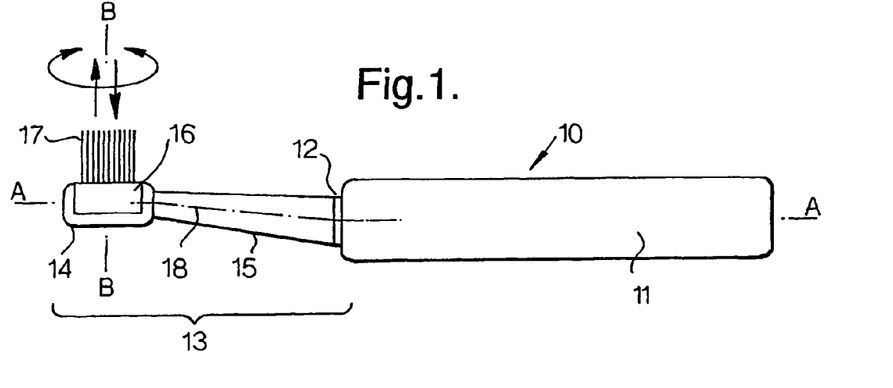
FIG. 1 shows the overall schematic layout of an electric toothbrush having a brush part as described.

Referring to FIG. 1 an electric toothbrush is shown overall in side view 10. The toothbrush 10 comprises a handle 11 by which it may be held, and which includes a drive motor, batteries, controls etc. (not shown). The handle 11 is replaceably connected at link 12, suitably a bayonet connection, to a replaceable section 13 including a head 14 at the end of the section 13 remote from handle 11 and a neck part 15. The assembly of handle 11, replaceable section 13 and head 14 are disposed along the length direction A-A of the toothbrush 10. In the head 14 is mounted a brush part comprising a bristle holder 16, from which a cluster of bristles 17 extend in a general bristle direction B-B generally perpendicular to length A-A. The holder 16 is driven by the motor (not shown) via drive shaft 18 (shown generally) extending along inside the neck part 15. The bristle holder 16 is mounted on an axle (shown 18 in FIG. 3) in head 14 for oscillatory rotation about an axis passing through the centre of the bristle cluster 17 and parallel to the bristle direction B-B and for simultaneous reciprocal movement up and down this axis as shown by the arrows.

In use the holder 16 performs simultaneously an oscillatory, i.e. reversing, rotary motion about an axis of rotation parallel to bristle direction B-B and passing through the centre in plan of the cluster of bristles 17, and a reciprocal motion up and down along the bristle direction B-B. The amplitude of the oscillatory rotary motion is ca. 30° either side of a mean position, and the amplitude of the reciprocal motion is ca. 1.0 mm. Numerous drive mechanisms are known in the art to achieve such motion.

Figure 2:
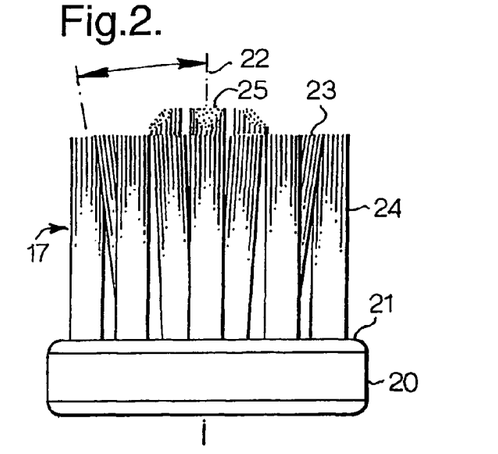
FIGS. 2 and 3 show a side and a plan view of a tuft cluster of the first aspect of this invention.
Figure 3:
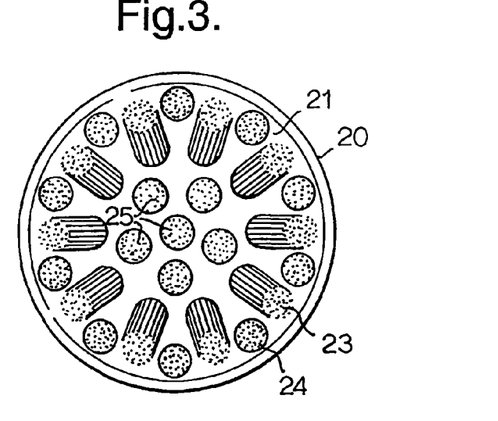

Referring to FIG. 2 a bristle holder 20 is shown in a side view. FIG. 3 shows a plan view looking down onto the surface 21, from which the bristle cluster 17 projects, along the rotation axis 22 about which the holder 20 rotates with oscillating rotation.

Mounted on the surface 21 are tufts of bristles 23, 24. These comprise first, outwardly leaning tufts 23 and second tufts 24 which are oriented parallel to the axis 22, i.e. perpendicular to surface 21. The tufts 23 all lean outwardly along a radius from rotation axis 22, making an angle of ca. 10° with the orientation of the axis 22 so that their distal ends are radially further from the rotation axis 22 than their bases. Being parallel to the axis 22, the distal ends of the second tufts 24 are at the same radial distance from the axis 22 as their bases.

The bases of tufts 23, 24 are arranged in two respective regular polygons each concentric around the rotation axis 22. The bases of all the first tufts 23 are radially inward of the bases of all the second tufts 24 so that the polygon of the bases of the first tufts 23 lies within and concentric with the polygon of bases of the second tufts 24. There are ten tufts 23 and ten tufts 24 in the respective polygons but there may be more or less bases in each polygon.

It is also seen that outwardly leaning first tufts 23 are arranged radially inward from gaps between adjacent second tufts 24 so that an outwardly leaning tuft 23 leans outwardly between flanking pairs of second tufts 24, and similarly a second tuft 24 extends parallel to the axis 22 between flanking pairs of outwardly leaning first tufts 23.

Figure 10:
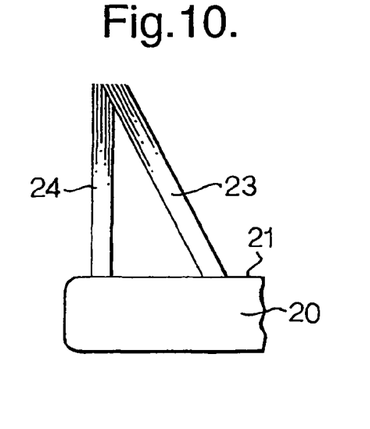
FIGS. 10, 11, 12 and 13 show part views of the clusters of FIGS. 2 to 9, and of another cluster of the first aspect of this invention.

FIG. 10 shows an arrangement similar to FIG. 2 and shows a view in the direction of a tangent to a circle radially mid way between the polygons of tufts 23 and 24. It is seen that the distal ends of tufts 24 are slightly further out radially than the distal ends of the tufts 23.

Figure 4:
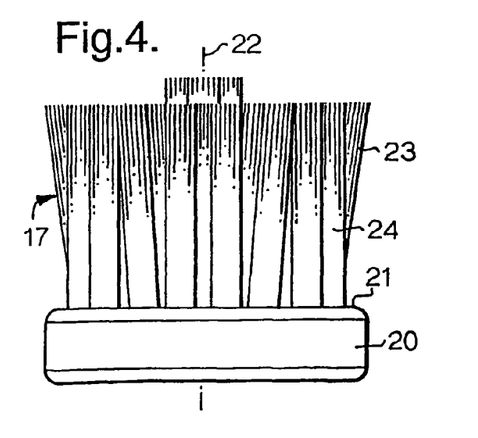
FIGS. 4 and 5 show a side and a plan view of another tuft cluster of the first aspect of this invention.
Figure 5:
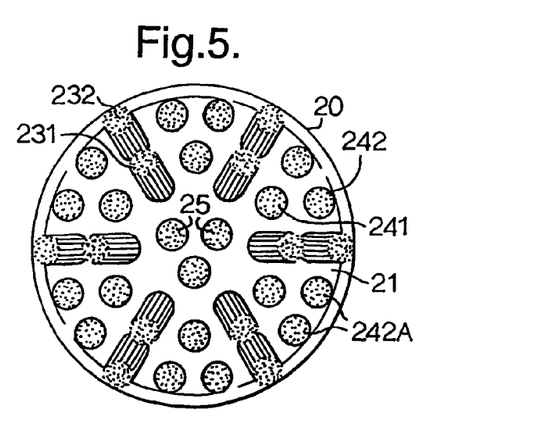

Referring to FIG. 4 a bristle holder 20 is shown in a side view looking perpendicular to the rotation axis 22. FIG. 5 shows a plan view looking down onto the surface 21, from which the bristle cluster 17 projects, along the rotation axis 22.

Mounted on the surface 21 are tufts of bristles 23, 24. These comprise first, outwardly leaning tufts 23 and second tufts 24 which are oriented parallel to the axis D-D, i.e. perpendicular to surface 21. The tufts 23 all lean outwardly along a radius from rotation axis 22, making an angle of ca. 10° with the orientation of the axis 22 so that their distal ends are radially further from the rotation axis 22 than their bases. Being parallel to the axis 22, the distal ends of the second tufts 24 are at the same radial distance from the axis 22 as their bases. The relative leaning of the tufts 23, 24 is thus similar to FIGS. 2 and 3.

The cluster shown in FIGS. 4 and 5 comprises two polygons of first tufts 231, 232, one 231 within the other 232, concentrically about the rotation axis 22, having their first tufts 231, 232 leaning outwardly at the same angle of ca. 8° relative to the rotation axis 22. The first tufts 231, 232 are arranged on radii from the rotation axis 22. In the arrangement shown there are also two polygons of second tufts 241, 242, one 241 within the other 242, the second tufts 241, 242 being oriented parallel to the axis 22. The arrangement therefore comprises, proceeding radially outward from the rotation axis 22: a polygon of bases of first tufts 231; a polygon of bases of second tufts 241 oriented parallel to the rotation axis; another polygon of bases of first tufts 232; another polygon of bases of second tufts 242 oriented parallel to the rotation axis.

Each polygon of first tufts 231, 232 contains six tufts so the polygon is a hexagon. The inner polygon of second tufts 241 also contains six tufts. The outer polygon of second tufts 242 contains twelve tufts so is a dodecagon. It is also seen that the outermost second tufts 242 are arranged in groups, i.e. pairs 242A, of circumferentially adjacent second tufts 242, so that first tufts 231 are circumferentially between circumferentially adjacent pairs of these groups of second tufts 242.

Figure 11:
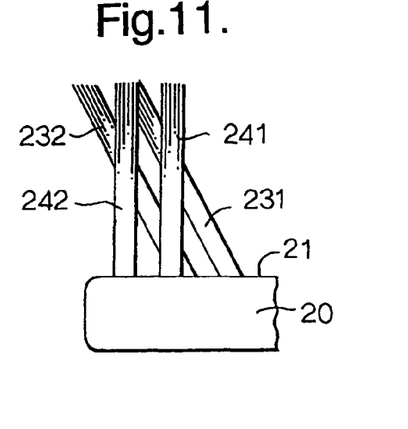

FIG. 11 shows an arrangement similar to FIGS. 4 and 5, showing a view in the direction of a tangent to a circle radially mid way between the polygons of tufts 241 and 242. It is seen that the distal ends of the tufts 231 are further out radially than the distal ends of the tufts. 241, and that the distal ends of tufts 232 are slightly further out radially than the distal ends of the tufts 242.

Figure 6:
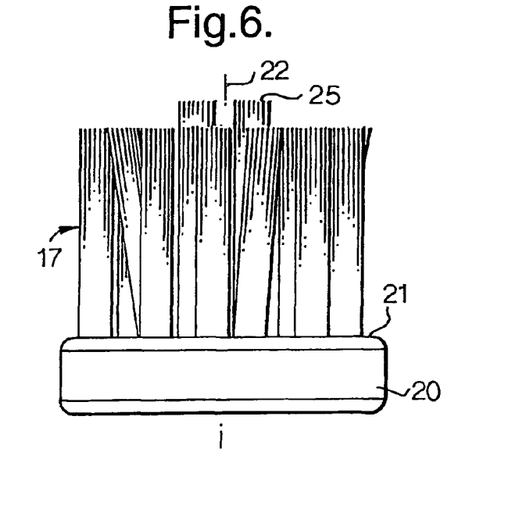
FIGS. 6 and 7 show a side and a plan view of another tuft cluster of the first aspect of this invention.
Figure 7:
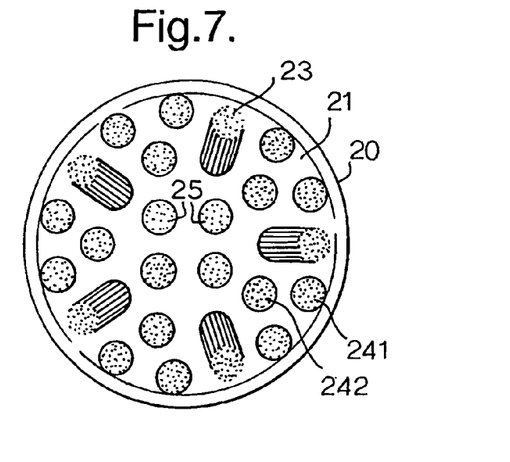

Referring to FIG. 6 a bristle holder 20 is shown in a side view looking perpendicular to the rotation axis 22. FIG. 7 shows a plan view looking down onto the surface 21, from which the bristle cluster 17 projects, along the rotation axis 22.

Mounted on the surface 21 are tufts of bristles 23, 241, 242. These comprise first, outwardly leaning tufts 23 and second tufts 241, 242 which are oriented parallel to the axis D-D, i.e. perpendicular to surface 21. The arrangement is similar to FIGS. 2 and 3 above. First tufts 23 are arranged in a regular pentagon, and second tufts 241, 242 are arranged in two polygons having respectively their bases further radially out 241, and at the same distance out 242 from the rotation axis than the bases of the first tufts 23, and aligned parallel to the rotation axis. In the outer polygon of second tufts 241 the tufts are arranged in circumferentially adjacent groups, i.e. pairs.

Figure 8:
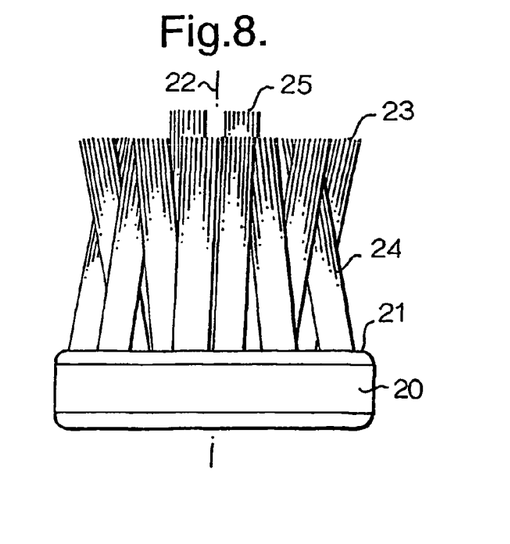
FIGS. 8 and 9 show a side and a plan view of another tuft cluster of the first aspect of this invention.
Figure 9:
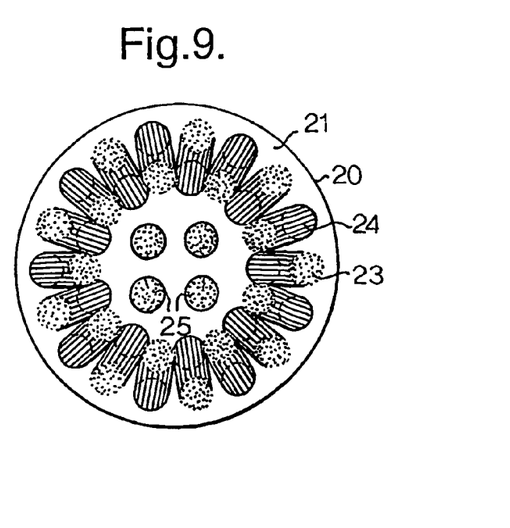

Referring to FIG. 8 a bristle holder 20 is shown in a side view looking perpendicular to the rotation axis 22. FIG. 9 shows a plan view looking down onto the surface 21, from which the bristle cluster 17 projects, along the rotation axis 22.

Mounted on the surface 21 are tufts of bristles 23, 24. These comprise first, outwardly leaning tufts 23, which all lean outwardly along a radius from rotation axis 22, making an angle of ca. 12° with the orientation of the axis 22 so that their distal ends are radially further from the rotation axis 22 than their bases. The cluster also comprises second inwardly leaning tufts 24, which all lean inwardly along a radius toward rotation axis 22, making an angle of ca. 11° with the orientation of the axis 22 so that their distal ends are radially closer to the rotation axis 22 than their bases.

The bases of tufts 23, 24 are arranged in two respective regular polygons each concentric around the rotation axis 22. The bases of all the first tufts 23 are radially inward of the bases of all the second tufts 24 so that the polygon of the bases of the first tufts 23 lies within and concentric with the polygon of bases of the second tufts 24. There are nine tufts 23 and nine tufts 24, so the polygons are nonagons, but there may be more or less bases in each polygon.

It is also seen that outwardly leaning first tufts 23 are arranged radially inward from gaps between adjacent second tufts 24 so that an outwardly leaning tuft 23 leans outwardly between flanking pairs of second tufts 24, and similarly a second tuft 24 extends parallel to the axis 22 between flanking pairs of outwardly leaning first tufts 23.

Figure 12:
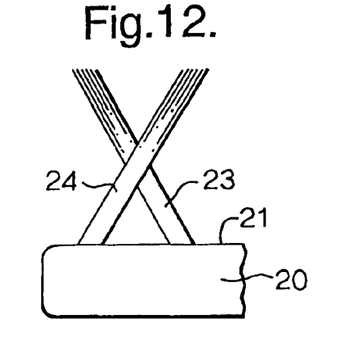

FIG. 12 shows an arrangement similar to FIGS. 8 and 9, showing a view in the direction of a tangent to a circle radially mid way between the polygons of tufts 23 and 24. It is seen that the distal ends of tufts 23 are further out radially than the distal ends of the tufts 24, and that as seen superimposed upon each other the tufts 23, 24 are seen to cross.

FIGS. 2-9 also show the presence of other, third, tufts of bristles 25. Although these are shown oriented parallel to the axis 22 they may alternatively lean inwardly toward or outwardly from the rotation axis 22. Such bristles 25 may be arranged at other points on the surface 21 to that shown, for example to increase the packing density of the bristle cluster. In the arrangements shown these third tufts 25 form an innermost polygon of tufts arranged around the axis of rotation 22, and extend further from the surface 21 than do the first and second tufts 23, 24, which all have their distal ends at the same perpendicular distance from surface 25.

All or some of the tufts of bristles 23, 24, 25 may also include a component of lean (not shown) in and/or against the direction of rotation of the holder 20 about axis 22.

Figure 13:
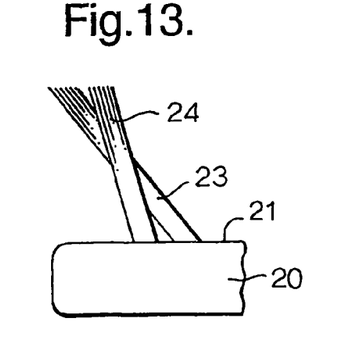

FIG. 13 shows another arrangement of first 23 and second 24 tufts, in which first tufts 23 project from surface 21 of the bristle holder 20, having their bases arranged in a polygon (not shown) around the rotation axis, leaning outwardly away from the rotation axis so that their distal end is further out from the rotation axis than their base. In the arrangement second tufts 24 also lean outwardly away from the rotation axis so that their distal end is further out from the rotation axis than their base, and their base is further radially out from the rotation axis than the bases of the first tufts 23, but the tufts 24 have a lesser angle of lean relative to the rotation axis than the first tufts 23. The view of FIG. 13 is at a tangent to a circle radially mid-way between the bases of the tufts 23, 24 and as seen superimposed upon each other the tufts 23, 24 are seen to cross.

Figure 14:
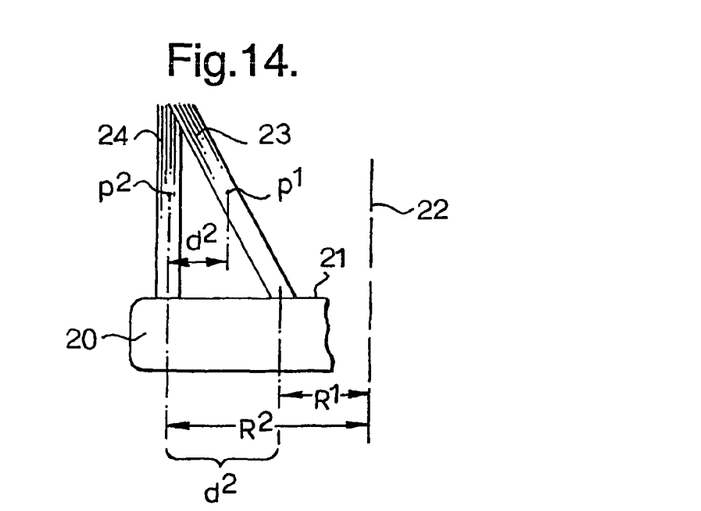
FIG. 14 shows a part view of a cluster of the first aspect of this invention.

Referring to FIG. 14, a plurality of first tufts 23 project from the surface 21 of the bristle holder 20, and have their bases arranged in a polygon around the rotation axis 22 as in the embodiments illustrated above. The first tufts 23 lean outwardly away from the rotation axis 22 so that their distal end is further out from the rotation axis 22 than their base.

There is also a plurality of second tufts 24 which also have their bases arranged in a polygon around the rotation axis 22 as in the embodiments illustrated above. In FIG. 14 the second tufts 24 are oriented parallel to the rotation axis 22, but they could lean as in the other illustrated embodiments.

The first 23 and second 24 tufts have their bases at different radial distances $R^1$, $R^2$ from the rotation axis D-D, $R^1$ being less than $R^2$, with a difference $R^2$ minus $R^1$ being $d^1$. The first 23 and second 24 tufts are oriented relative to the rotation axis 22 such that at a point, e.g. $P^1$, $P^2$ along their base-distal end length the first 23 and second 24 tufts are respectively at radial distances from the rotation axis 22 with a difference $d^2$ in their respective radial distances less than the difference $d^1$ in the radial distances $R^1$, $R^2$ of their bases from the rotation axis 22. It is seen that the difference $d^2$ is minimal at the distal ends on the tufts 23, 24. The same principle is seen to apply to the embodiments illustrated in FIGS. 10-13, and in FIGS. 11, 12 and 13 it is seen that $d^2$ drops to zero at a point as the tufts 23, 24 are at the same radial distances from the rotation axis 22, but proceeding further in the base-distal direction $d^2$ again increases as the tufts 23, 24 diverge in their radial distance.

FIGS. 15-20 illustrate a brush part according to the second aspect of this invention.

Figure 15A:
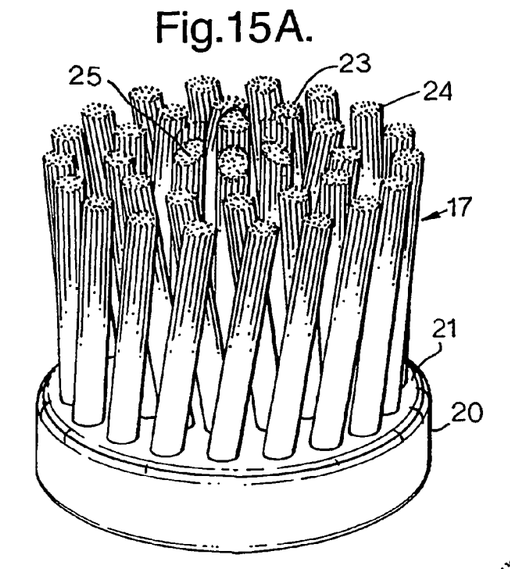
FIGS. 15A, 15B and 15C respectively show two perspective views and a plan view of a bristle cluster of the second aspect of this invention.
Figure 15B:
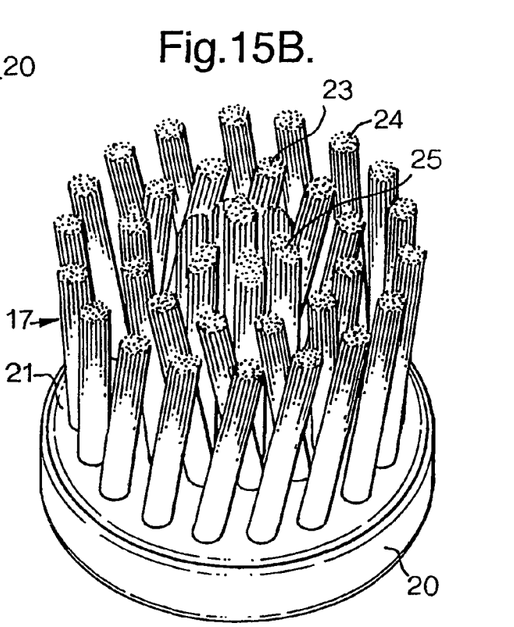
Figure 15C:
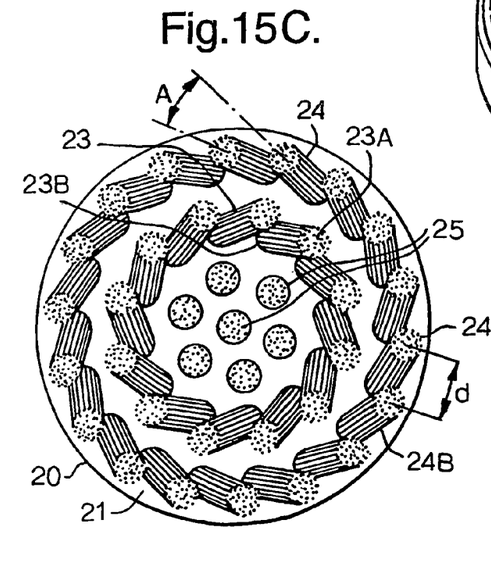

Referring to FIG. 15, FIGS. 15A and 15B show perspective views of a bristle holder 20, on a surface 21 of which a bristle cluster 17 is mounted. FIG. 15C shows a plan view of the cluster 17 and holder 20, looking down on surface 21 along the axis 22 about which holder 20 rotates with oscillating rotation.

As seen in FIGS. 15A, 15B and 15C, the cluster 17 comprises a plurality of tufts of bristles arranged in two regular polygons of tufts, viz. a first, inner polygon 23 of twelve tufts and a second outer polygon 24 of eighteen tufts surrounding the inner polygon 23. Both the inner 23 and outer 24 polygons are arranged around a common centre. In both polygons 23, 24 all of the tufts are mounted inclined at an angle such that the distal end 23A, 24A of the tuft (furthest from the surface 21 of the bristle holder 20) is further around the polygon which contains it than the opposite base end 23B, 24B of the tuft mounted in the surface 21, by the distance "d" shown in FIG. 15C. In these inner 23 and outer 24 polygons their respective inclined tufts are inclined in opposite directions around the polygons 23, 24, such that the tufts in the inner polygon 23 are inclined in a clockwise direction, whilst the tuft(s) in the outer polygon 24 are inclined in an anti-clockwise direction. The tufts in both polygons 23, 24 are inclined at ca. 75° to the flat surface 21 of the bristle holder 20.

The tufts 23, 24 are also aligned outwardly angled relative to the centre of the polygon as viewed in plan, relative to the direction of an adjacent side of the polygon, by the angle A seen in FIG. 15C.

The cluster 17 also includes a polygon 25 of six third bristles having a common centre with the polygons 23, 24, situated within and surrounded by the inner polygon 23. The tufts of this third polygon 25 are substantially parallel to the axis of rotation 22 of the holder 20. At the centre of all three of the polygons 23, 24, 25 is a single third tuft 26, also aligned substantially parallel to the axis of rotation 22.

As viewed in plan, the clusters 17 of FIGS. 15, 16, 17 and 18 are identical, but these clusters differ in the profile of the ends of the tufts remote from the surface 21 of the bristle holder 20.

Figure 16A:
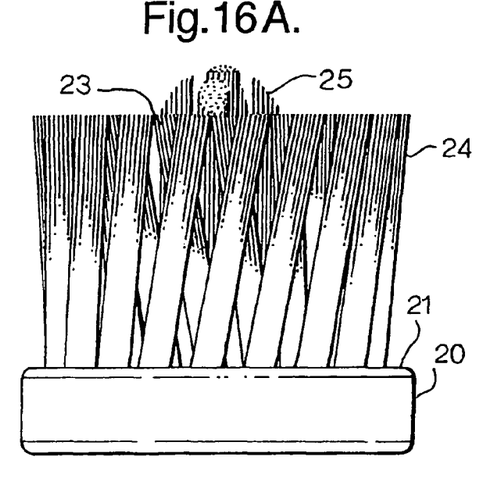
FIGS. 16A, 16B and 16C respectively show a side, perspective and plan view of another bristle cluster of the second aspect of this invention.
Figure 16B:
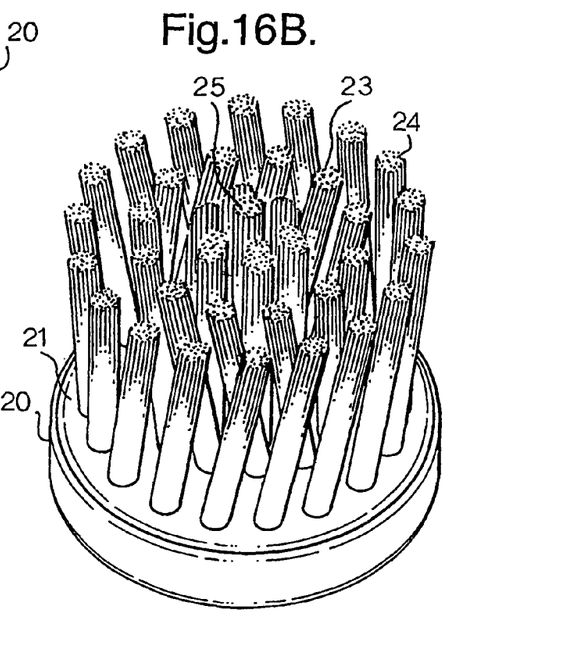
Figure 16C:
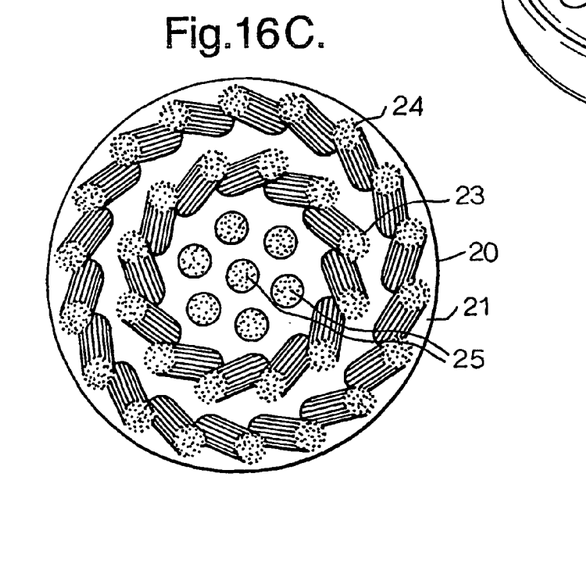
Figure 17A:
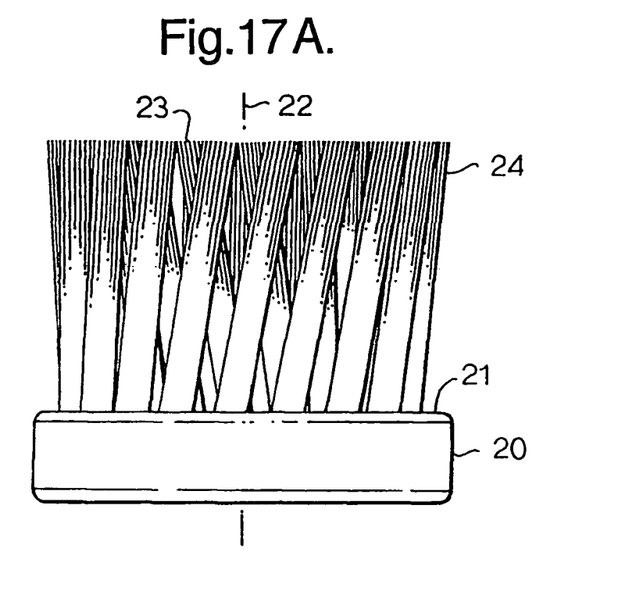
FIGS. 17A and 17B respectively show a side and perspective view of another bristle cluster of the second aspect of this invention.
Figure 17B:
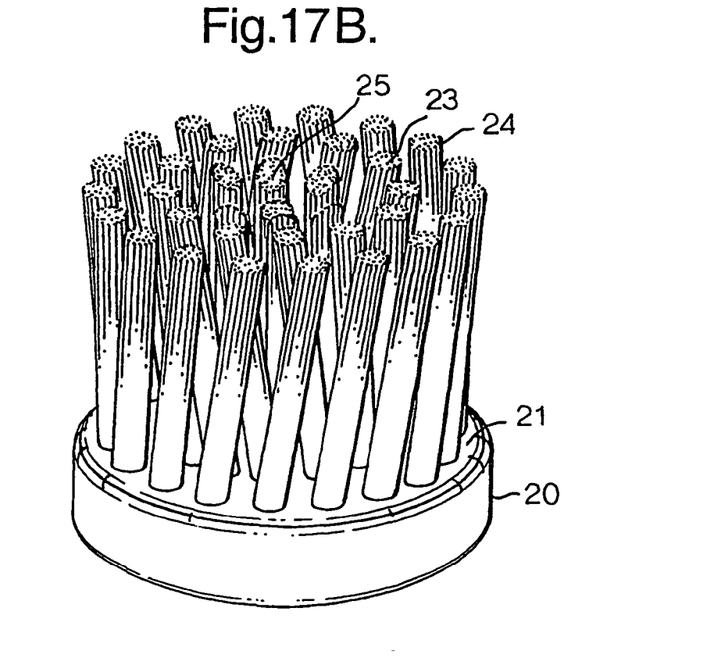

In FIGS. 15, 16 and 17 the ends of the two outer polygons 23, 24 are cut so as to lie in a plane parallel to the bristle surface 21.

In FIG. 15 the ends of the tufts of the innermost polygon 25 and the central tuft 26 are profiled to form a peak about the centre of the cluster 17. The ends of the tufts of the innermost polygon 25 are cut so as to incline upwards toward the centre 22 of the polygon in a generally conical shape with its apex pointing away from the bristle surface 21.

FIG. 16 shows a similar arrangement, but with the ends of the tufts of the innermost polygon 25 profiled into a generally hemispherical dome shape.

In FIG. 17 the ends of the tufts of the tufts of the innermost polygon 25 are profiled to incline downwards toward the centre 22 of the polygons 23, 24, 25 in a generally conical shape with its apex pointing toward the bristle surface 21.

Figure 18A:
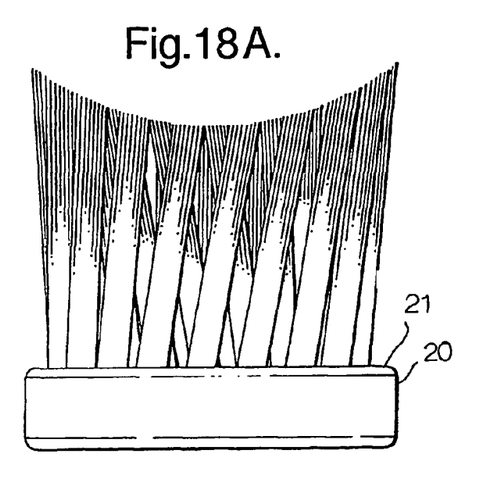
FIGS. 18A, 18B and 18C respectively show two side views and a perspective view of another bristle cluster of the second aspect of this invention.
Figure 18B:
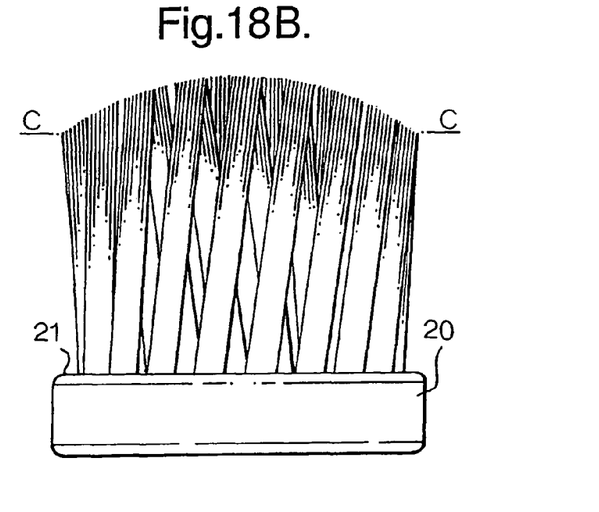
Figure 18C:
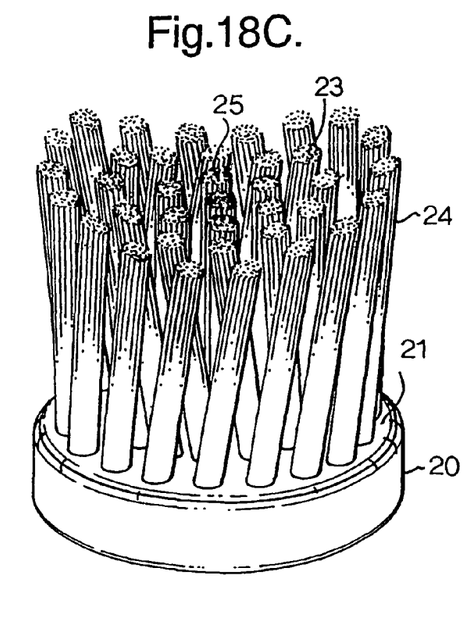

In FIG. 18 the ends of all of the tufts 23, 24, 25, 26 are profiled in a concave cylindrical surface having the longitudinal axis of the cylinder C-C aligned perpendicular to the axis of rotation 22.

Figure 19A:
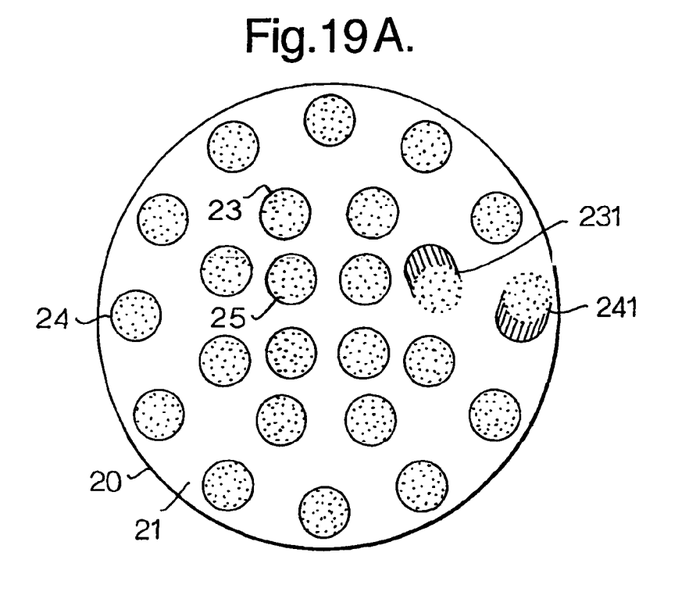
FIGS. 19A and 19B respectively show a plan view of and a section through another bristle cluster of the second aspect of this invention.
Figure 19B:
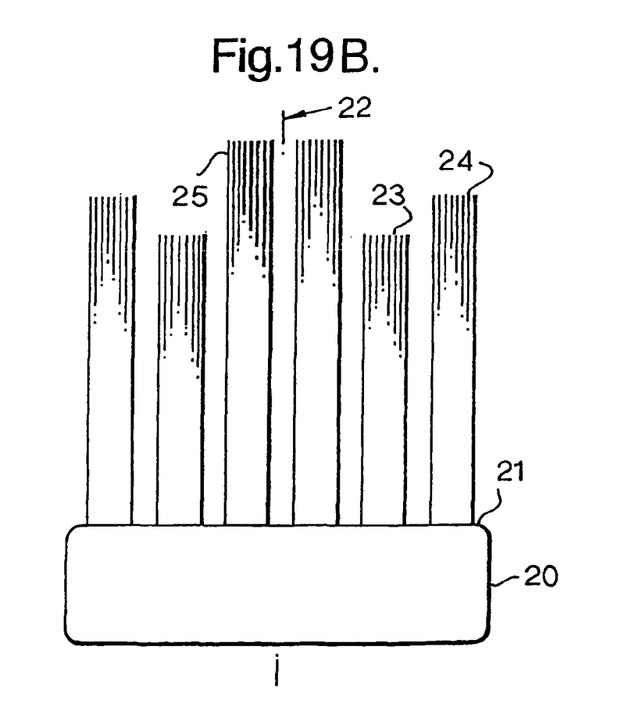

Referring to FIG. 19, FIG. 19A shows a plan of the arrangement of tufts of bristles, and FIG. 19B shows a section through the cluster parallel to the axis of rotation. As seen in FIG. 19A the cluster 17 comprises a plurality of tufts of bristles arranged in two regular polygons, viz. a first, inner polygon 23 of eight tufts and a second outer polygon 24 of twelve tufts surrounding the inner polygon 23. Both the polygons 23, 24 are arranged around a common centre being rotation axis 22. In both polygons 23, 24 all of the tufts are mounted inclined at an angle such that the distal end of the tufts are further around the polygon which contains them than the base end, the inclination of only one tuft 231, 241 in each of the polygons 23, 24 being shown in FIG. 19A which is a projection on a plane perpendicular to the axis of rotation 22. In these inner 23 and outer 24 polygons their respective inclined tufts are inclined in opposite directions around the polygons 23, 24, such that the tufts in the inner polygon 23 are inclined in a clockwise direction, whilst the tufts in the outer polygon 24 are inclined in an anti clockwise direction. The tufts in polygons 23, 24 are also aligned outwardly angled relative to the centre 22 of the polygon, relative to the direction of an adjacent side of the polygon.

The cluster 17 also includes an innermost polygon 25 of four third bristles in a regular square having a common centre with the polygons 23, 24, the tufts of third polygon 25 being substantially parallel to the axis of rotation 22 of the holder 20.

As seen in the sectional view of FIG. 19B, being a sectional view through the bristle cluster 17 cut through rotation axis 22, the ends of the tufts 23, 24, 25 are profiled to form a peak about the centre of the cluster, the tufts of the innermost polygon 25 being the highest, the tufts of intermediate polygon 23 being lower than both the tufts of the outermost 24 and innermost 25 polygons, so that the height of the polygons dips between the outermost 24 and innermost 25 polygons.

Figure 20A:
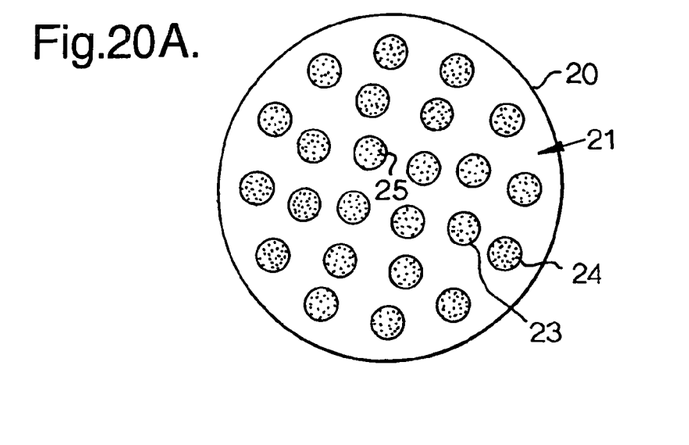
FIGS. 20A, 20B and 20C respectively show a plan at the bristle surface, a plan view and a side view of another bristle cluster of the second aspect of this invention.
Figure 20B:
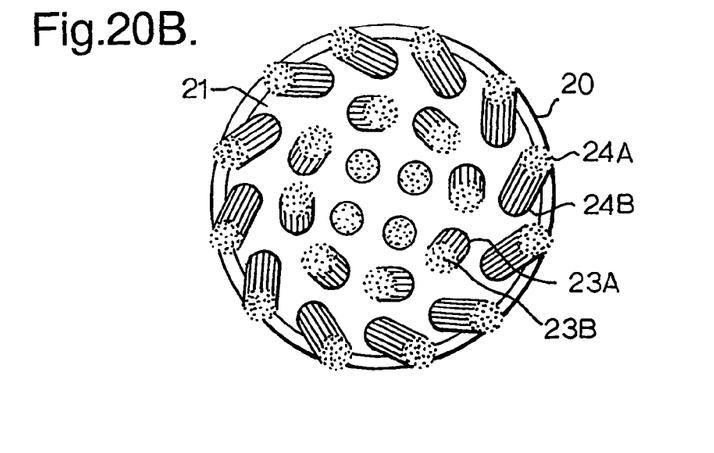
Figure 20C:
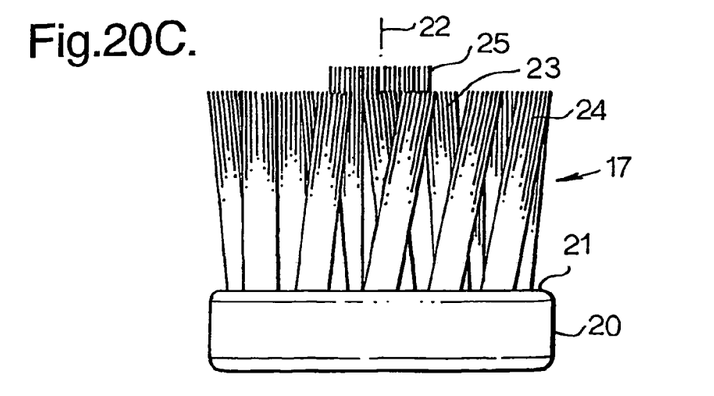

Referring to FIG. 20, FIG. 20A shows a plan of the arrangement of tufts of bristles at the bristle surface 21. FIG. 20B shows a plan view of the cluster looking down the rotation axis 22 onto the surface 21. FIG. 20C shows a side view perpendicular to the axis of rotation 22. As seen in FIGS. 20A and 20B the cluster 17 comprises a plurality of tufts of bristles arranged in two regular polygons, a first inner regular polygon 23 of eight tufts and a second outer regular polygon 24 of twelve tufts surrounding the inner, polygon 23, both polygons 23, 24 being arranged around a common centre.

As seen in FIG. 20B in both polygons 23, 24 all of the tufts are mounted inclined at an angle such that the distal end 23A, 24A of the tuft is further around the polygon which contains it than the opposite base end 23B, 24B of the tuft, the respective inclined tufts being inclined in opposite directions around the respective polygons 23, 24. In two versions of the FIG. 20 embodiment the inclination of the tufts of the outer polygon is 8° or 10°, and the respective inclination of the tufts of the inner polygon is 4° or 5° in the opposite direction. The tufts of the outer polygon 24 are also aligned outwardly at an angle 5° relative to the centre of the polygon as viewed in plan, relative to the direction of an adjacent side of the polygon, whilst the tufts 20 of the inner polygon 24 are aligned parallel to the direction of an adjacent side of the polygon.

The cluster 17 also includes an innermost polygon 25 of four third bristles in a regular square having a common centre with the polygons 23, 24, the tufts of which are substantially parallel to the axis of rotation 22 of the holder 20, and the distal ends of the which are higher than the tufts 23, 24, the ends of which lie in a plane. The height of the tufts 24 above surface 21 is 8 mm and of the tufts 23, 24 is 6 mm.

The invention claimed is:

1. A brush part for an electric toothbrush which includes a bristle holder mounted for rotary motion about a rotation axis, a plurality of first tufts projecting from a surface of the bristle holder and having their bases arranged in a polygon around the rotation axis and leaning outwardly away from the rotation axis at an acute angle so that their distal end is further out from the rotation axis than their base, and a plurality of second tufts projecting from a surface of the bristle holder and which have their bases further radially out from the rotation axis than the bases of the first tufts and having their bases arranged in a polygon around the rotation axis, wherein the second tufts either:

are aligned parallel to the rotation axis, or;

lean inwardly at an acute angle relative to the rotation axis toward the rotation axis so that their distal ends are at less distance radially from the rotation axis than their base, or;

lean outwardly at an acute angle relative to the rotation axis and away from the rotation axis so that their distal end is further out from the rotation axis than their base, but at a lesser angle of lean relative to the rotation axis than the first tufts, and wherein the distal ends of the first tufts are at a further radial distance from the rotation axis than the distal ends of the second tufts.

2. The brush part according to claim 1 wherein the respective bases of the first and second tufts are circumferentially adjacent to each other on a circle centered on the rotation axis.

3. The brush part according to claim 1 wherein the polygon of bases of the second tufts lies outside and is concentric with the polygon of bases of the first tufts.

4. The brush part according to claim 3 wherein a first tuft is radially adjacent to a gap between two circumferentially adjacent second tufts, and the first tuft leans outwardly between circumferentially adjacent pairs of second tufts.

5. The brush part according to claim 4 wherein there are the same numbers of respectively first and second tufts in the respective inner polygon of first tufts and the outer polygon of second tufts.

6. The brush part of claim 1 wherein outwardly leaning first tufts and outwardly leaning second tufts lean respectively outwardly along radii centered at the rotation axis.

7. The brush part according to claim 1 wherein the angle axis at which the outwardly leaning first tufts lean is between 2.5 to 35°.

8. The brush part according to claim 7 wherein the angle at which the outwardly leaning first tufts lean is between 5 to 10°.

9. The brush part according to claim 8 wherein the angle at which the outwardly leaning first tufts lean is between 8 to 10°.

10. The brush part according to claim 1 wherein the angle at which the outwardly leaning first tufts lean is between 2.5 to 35°, and the second tufts lean inwardly at an acute angle of between 2.5 to 35° relative to the rotation axis relative to the rotation axis toward the rotation axis so that their distal ends are at less distance radially from the rotation axis than their base.

11. The brush part of claim 1 wherein outwardly leaning first tufts lean outwardly along radii centered at the rotation axis, and inwardly leaning second tufts lean inwardly along radii centered at the rotation axis.

12. An electric toothbrush provided with the brush part according to claim 1.

* * * * *